United States Patent [19]

Nagy et al.

[11] 4,143,554
[45] Mar. 13, 1979

[54] ULTRASONIC SCANNER

[75] Inventors: Art Nagy, Santa Monica; Andrew P. Proudian, Chatsworth, both of Calif.

[73] Assignee: Second Foundation, Woodland Hills, Calif.

[21] Appl. No.: 833,244

[22] Filed: Sep. 14, 1977

Related U.S. Application Data

[63] Continuation-in-part of Ser. No. 777,146, Mar. 14, 1977, abandoned.

[51] Int. Cl.$^2$ ............................................. G01N 79/04
[52] U.S. Cl. ...................................... 73/641; 73/620;
    73/626; 73/642; 73/644; 128/2 V
[58] Field of Search ................. 73/620, 621, 622, 626,
    73/627, 628, 629, 632, 633, 641, 642; 128/2 V;
    310/327, 335, 336

[56] References Cited

U.S. PATENT DOCUMENTS

| 2,483,821 | 10/1949 | Firestone | 73/644 X |
| 3,269,173 | 8/1966 | von Ardenne | 73/620 X |
| 3,362,501 | 1/1968 | Lenahan | 73/632 X |
| 3,687,219 | 8/1972 | Langlois | 73/644 |

FOREIGN PATENT DOCUMENTS

| 2601559 | 7/1976 | Fed. Rep. of Germany | 73/620 |
| 2529112 | 1/1977 | Fed. Rep. of Germany | 73/633 |
| 01001977 | 1/1977 | Fed. Rep. of Germany | 73/633 |
| 184000 | 12/1966 | U.S.S.R. | 73/642 |

OTHER PUBLICATIONS

G. Kossoff et al., Ultrasonic Two-Dimensional Visualization for Medical Diagnosis, J.A.S.A., Nov. 1968, pp. 1310–1317.

J. P. Bacon, New Developments in Ultrasonic Transducers and Their Application to Non-Destructive Testing, Non Destructive Testing, May-Jun. 1961, pp. 184–187.

*Primary Examiner*—Richard C. Queisser
*Assistant Examiner*—John P. Beauchamp

[57] ABSTRACT

An ultrasonic scanner for producing a sector scan in an object to be examined in which one or more ultrasonic transducers traverse an arcuate path with respect to a reflector which is positioned to receive the ultrasonic waves scanning the surface of the reflector from each of the transducers and converge such waves at a point of a preselected distance in front of the reflector. In general, the ultrasonic waves are converged at a point outside the scanner and inside the object to produce a sector scan in the object having its center at the convergence point. In one embodiment of the scanner the reflector only partially reflects the ultrasonic waves and an additional stationary transducer is provided which is positioned to produce ultrasonic waves which radiate through the reflector and coincide with one of the lines of the sector scan, thus permitting simultaneous M-mode or pulse Doppler echo information to be obtained in perfect registration with the sector scan lines. Attenuation, absorption and anti-reflection means are provided to suppress echo artifacts.

33 Claims, 7 Drawing Figures

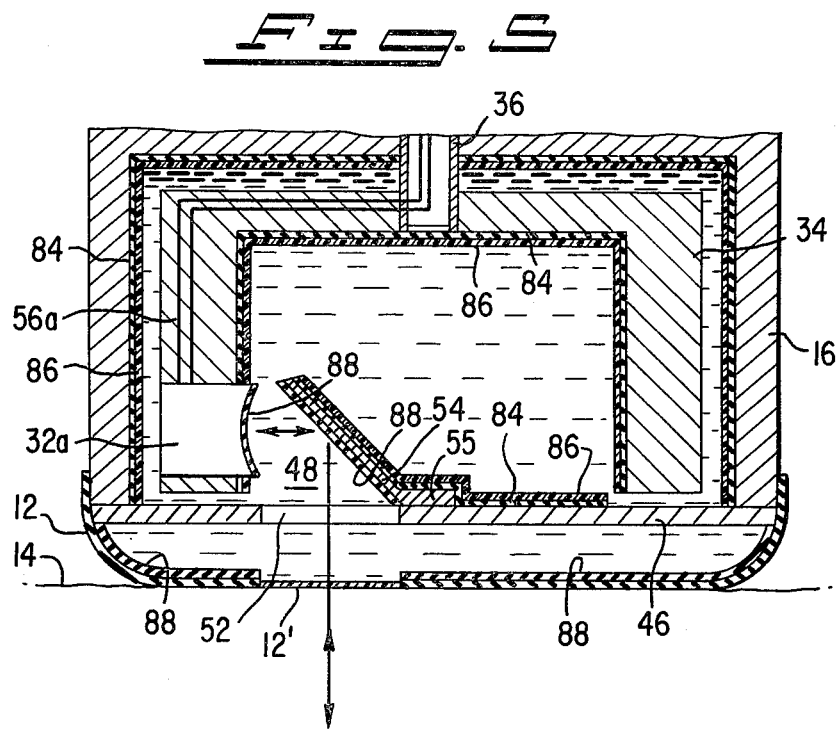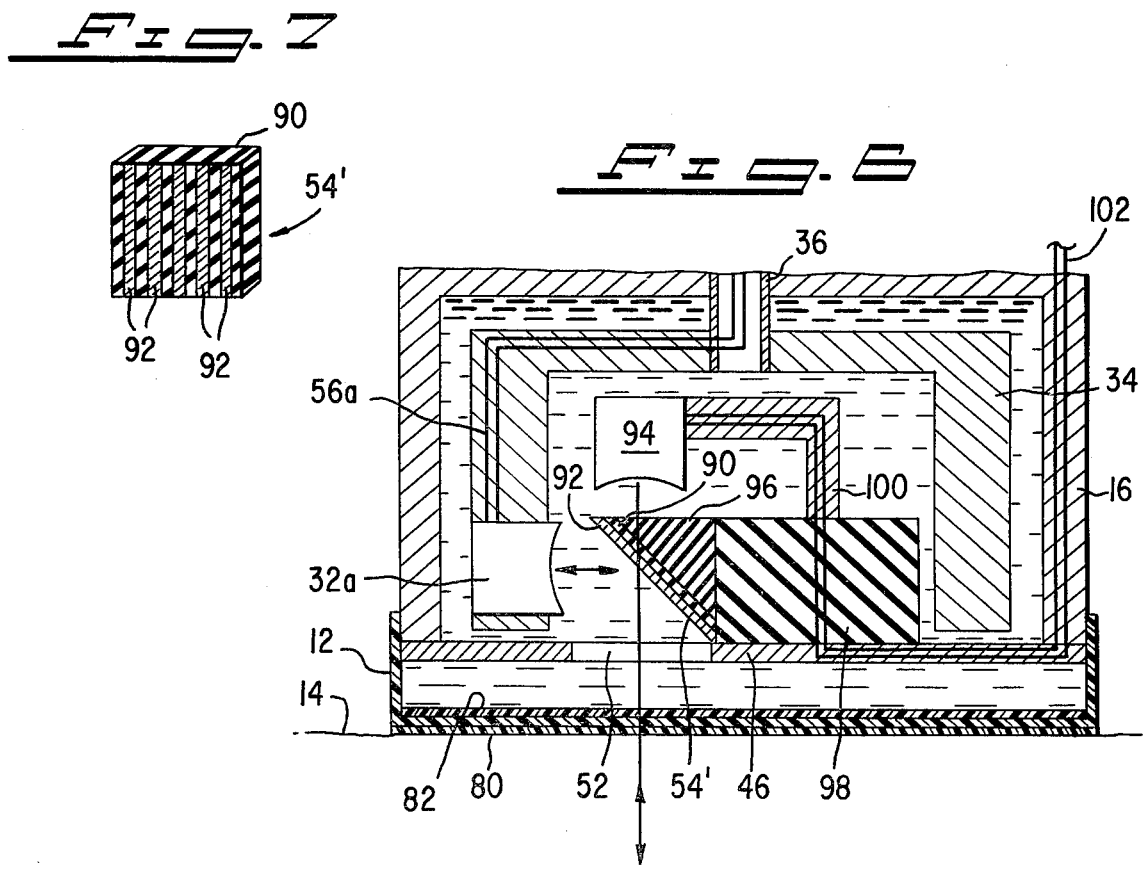

ULTRASONIC SCANNER

This is a continuation-in-part of application, Ser. No. 777,146, filed Mar. 14, 1977, now abandoned.

BACKGROUND OF THE INVENTION

1. Field of the Invention

The invention relates to the field of ultrasonic scanners and, in particular, to ultrasonic scanners for producing sector scans in an object to be scanned.

2. Prior Art

Dynamic cross-sectional echography (DCE) is a commonly used technique for producing sequential two-dimensional images of cross-sectional slices of the human anatomy by means of ultrasound radiation at a frame rate sufficiently high to enable dynamic visualization of moving organs. Apparatus utilizing DCE are generally called DCE scanners and transmit and receive short, ultrasonic pulses in the form of narrow beams or lines. The reflected signal strength as a function of time, which is converted to a position using a nominal sound speed, is displayed on a cathode ray tube, or other suitable device, in a manner somewhat analogous to radar or sonar displays. While DCE can be used to produce images of any object, it is frequently used for visualization of the heart and main heart vessels.

Existing DCE scanners can be classified according to the geometry of their field of view (linear or sector scanning), according to the means used for scanning that field of view (mechanical or electronic scanning), and according to whether the transducer scans the patient or object through an intervening water bath or by direct contact with the surface of the object as, for example, the skin of a patient using an appropriate contact gel or oil. Linear scanners produce a scan of the anatomy consisting of a set of nominally parallel scan lines, displaced with respect to one another by a line spacing roughly comparable to the effective width of each line, as determined primarily by the transducers used in the apparatus. The cross-section imaged by such scanners is therefore approximately rectangular in shape, its width being determined by the line spacing and total number of lines, while its depth is determined by the lesser of the useful penetration depth of the ultrasound radiation into the body and the unambigous range of the device. Linear scanners are generally used where there is a relatively extended region on the body surface from which access to the parts of interest of the anatomy is possible, as in the abdominal organs. Sector scanners produce a scan of the anatomy consisting of a fan of diverging lines spaced angularly from one another but intersecting (nominally) at a point. The angular spacing being even or uneven depending upon the apparatus and roughly comparable to the effective angular width of each line. The cross-section imaged by such scanners is therefore approximately wedge or pie-shaped, i.e., it is approximately a circular sector, the total angular width of the sector, or sector scan angle, being determined by the angular line spacing and total number of lines, and the sector radius being determined by the lesser of the useful penetration depth of the ultrasound radiation into the body and the unabigous range of the device. Sector scans are generally used where the anatomical window or region on the body surface from which access to the anatomical part of interest is relatively small, as in the adult heart, the brain and the eye in particular.

A large amount of work has gone into the development of DCE sector scanners. Existing direct contact sector scanners include both phased array and mechanical scanners. In phased array scanners such as those exemplified in articles by M. G. Maginness et al, "State-of-the-art in Two-dimensional Ultrasonic Tranducer Array Technology", Medical Physics, Vol. 3, No. 5, Sept./Oct. 1976, Von Ramm et al, "Cardio-Vascular Diagnosis in the Real Time Ultrasound Imaging", Acoustical Holography, Vol. 6, 1975, and J. Kisslo et al, "Dynamic Cardiac Imaging Using a Phased-Array Transducer System", published by Duke University, Durham, N.C., a large (16–60 element) linear array of small transducers is used, with a variable time (phase) delay inserted between elements of the array both in the transmission and reception of the ultrasound signal, resulting in a transmitted beam and a receiving beam or sensitivity pattern whose direction is determined by the magnitude of the inter-element time delay. In sector scanning using phased array scanners, such scanning is achieved without any mechanical motion of the transducer array which remains in stationary contact with, for example, the patient's skin. Such phased array scanners have, however, several severe practical limitations. One such limitation resides in the relative complexity of the multi-element transducer array and especially of the transmit/receive electronics necessary to achieve electronic beam steering, resulting in a relatively high cost of phased array scanners. In addition, the ultrasonic beam quality in phased array scanners, in terms of lateral resolution and side lobe levels and the possible occurance of grating lobes, is poor compared to that of single transducer scanners, particularly for beam direction angles greater than 30 degrees away from the normal to the transducer, limiting its useful scanning angles to about 60 degrees even though the beam might be steered beyond that limit. Another significant limitation of existing phased array scanners and all direct contact scanners is that the scanned section is centered at the center of the transducer face, essentially at the skin or surface of the object and therefore outside of the patient or object, so that in certain applications close-in structures are not well resolved, while in other applications anatomical structures can limit the field of view of the scanner. This is particularly the case in adult cardiac scanning, where the ultrasonic access window to the heart is generally in the second to fifth intercostal spaces, just to the left of the sternum. In that case, the ribs will tend to limit the scanner field of view, particularly in obese adult patients where the ribs are close to the patient's skin, so that the transducer window cannot readily be pressed into the intercostal space. It would be necessary, in order to avoid the rib interference problem, to have the center of the sector scan replaced somewhat inside the patient, in or near the space between the interfering ribs. Limitations of the scanning sector angle to values significantly below 90 degrees due to rib interference or beam steering limitations or both, can prevent, in many cases, visualization of the entire long dimension of the heart and can seriously affect the diagnostic value of DCE in cardiac examinations as well as in other examinations.

A further limitation of present phased array scanners is that they can only be dynamically focused in range in one lateral dimension, namely in the plane of scanning. Two-dimensional focusing would require a two-dimensional matrix or array of phased transducer elements and is beyond the present commercial state of the art.

Another class of sector scanners are mechanical in nature and can be divided into two classes, oscillating transducer scanners and rotating transducer scanners. An oscillating transducer scanner is exemplified by the scanner described by J. Griffith et al, "A Sector Scanner for Real Time Two-Dimensional Echocardiography", Circulation, Volume XLIX, June 1974, in which a single transducer is oscillated about an axis nominally lying in the front plane and passing through the center of the transducer with an appropriate angle sensor being used to monitor the angular position of the transducer at any time. Contact with the patient is maintained by the use of a gel, and in operation the patient's tissues must conform to the movement of the transducer which is essentially rigid. While the oscillating transducer scanner described by Griffith is of the direct contact variety, oscillating transducer scanners can also be of the non direct or water bath variety as described by A. Ashberg, "Ultrasonic Cinematography of the Living Heart", Ultrasonics, April, 1967, in which the internal structures of the human heart have been investigated by using the ultrasound pulse-echo method and an ultrasound optical mirror system immersed in a water tank having one wall consisting of a thin rubber membrane pressed against the chest wall of the patient through which ultrasonic energy can easily penetrate. These mechanical sector scanners also suffer from a number of limitations and drawbacks which limit their use. Both of the above described mechanical sector scanners suffer the same rib interference limitation as the phased array scanners. In addition, the direct contact mechanical sector scanners are limited in their useful scanning angle by the problems of the moving contact and physical angulation of the transducer away from the skin, in most cases to values of 30 to 45 degrees. A limitation common to both of the mechanical sector scanners described is that their angular rate of sweep is not uniform, since the transducer or mirror system must reverse direction at the end of each sweep in each direction, so that the line density is greatest at the edges of the sector, where it is usually least desirable, and is lowest at the center of the sector, i.e., the center of the region of interest. Concomitant with this limitation is the fact that the alternate direction of sweep means that an area at the end of a sweep is interrogated twice in a very short interval, as the scan crosses it in opposite directions, and is not interrogated again until nearly the duration of two frames. In addition, only the mid-point of the scan is interrogated at a constant frame rate. Another disadvantage of the direct contact of the oscillating transducer scanner described by Griffith arises from the physical transducer motion itself and includes patient discomfort, vibration of the transducer in the operator's hand, and mechanical wear of the transducers moving parts which are subjected to significant forces.

A further limitation of direct contact scanners, including phased array scanners, arises from near field non-uniformities in the so-called Fresnel zone of the transducer or array. As is well known, the acoustic pressure field for an unfocused transducer exhibits large scale oscillations, including a series of peaks and nulls, within a distance $D = r^2/\lambda$ from the face of the transducer, where r is the effective radius of the transducer, or array, and $\lambda$ is the wavelength. Since the region within a distance D/2, which is referred to herein as the "near" Fresnel zone is characterized by particularly large fluctuations in amplitude both laterally and in range, target positions and strengths will be falsely displayed as a sector scan is carried out in that region. For typical transducer radius to wavelength ratio of 10, and typical wavelengths of 0.7mm, the length D/2 of the near Fresnel region, extends 3.5 centimeters in front of the transducer, and this will frequently include portions of the body which are of diagnostic interest.

Another type of mechanical sector scanner is the rotational scanner described by Barber et al, "Duplex Scanner II: For Simultaneous Imaging of Artery Tissues and Flow", IEEE, 1974 Ultrasonics Symposium Proceedings, and by Daigle et al, "A Duplex Scanning System for Pediatric Cardiology", Proceedings 1st Meeting of World Federation for Ultrasound in Medicine and Biology, 1976, which uses a set of transducers mounted on a rotor coupled to the patient through a water column which is separated from the skin surface by a thin silastic or rubber membrane. While the rotating transducer water bath scanner described by Barber, called the "Duplex Echo-Doppler Scanner" permits a stationary contact with the patient and provides a uniform beam spacing or line density as well as uniform sampling, it is severely limited in its application to adult cardiac scanning by the fact that the center or axis of the sector scan is removed or offset from the skin surface by a distance equal to the sum of the rotating scanner radius and the length of the water column, resulting in a severe rib interference problem. The device of Barber et al, is primarily intended for use in pediatric cardiology where rib interference is not serious.

A further limitation of all present mechanical scanners is that they cannot provide a simultaneous M-mode or Doppler scan of any selected line of the scanned sector at rates adequate for measurements of heart valve and heart wall motions. While any line of the sector scan of a mechanical scanner can be sampled at the frame rate of the sector scan itself, typically 20 to 45 frames per second and displayed on an M-mode type display, this rate is too slow since a minimum of 300 frames per second is necessary in order to resolve rapid motions, such as the motion of the mitral valve of the heart, with existing M-mode single beam echocardiographic probes operating at frame rates in excess of 1000 frames per second. In addition, even if such rates could be attained by a mechanical scanner, the unambiguous range, or useful penetration, corresponding to a frame rate of 300 or more frames per second of the 80 to 100 lines typically forming a sector scan would be less than two centimeters, and therefore totally useless. One attempt to provide a Doppler scan in a mechanical scanner is shown in the rotational scanner described by Barber in which an auxiliary transducer operated in the pulsed Doppler mode is provided which permits obtaining information about velocities of blood flow and movement of cardiac structures essentially simultaneously (within less than a millisecond) with the echoamplitude information. However, the Doppler scan in the device described by Barber is not centered around the same point as the echo scan, since the transducer is mounted off to the side of the echo scanning head. Thus, the point of entry of the Doppler beam and the corresponding interrogated volume are different than the point of entry of the echo sounding beam and its corresponding interrogated volume, creating problems both of access and of interpretation as the same line as one of the sector lines is not simultaneously sampled.

The image producing capabilities of current ultrasonic scanners are further limited by the existence of "echo" artifacts which degrade the quality of and complicate the interpretation of the reflected signals from the object being visualized. Such echo artifacts are caused by ultrasound energy being received by a detector which energy is not directly reflected from the body or target under examination. In a system utilizing mirrors and membranes, such as described by Asberg, a portion of the echo artifacts are caused by partial reflection of acoustic pulses along the path of the desired or "target" echoes by the membranes and the mirrors before they reach the body or target under examination. Another portion of the echo artifacts are caused by partial reflection of acoustic pulses from the membranes and mirrors not along the return path of the target echoes but along other paths resulting in reflections from numerous internal surfaces which eventually inpinge upon the detector. A further portion of the echo artifacts results from stray acoustic radiation that is not intercepted by the membranes or mirrors but merely reflects around the scanner with some of it reaching the detector and producing false echoes.

Accordingly, it is a general object of the present invention to provide an improved ultrasonic sector scanner.

It is another object of the present invention to provide a sector which has a sector scan center of focus which can be located in front of the scanner so as to minimize interference problems.

It is a further object of the present invention to provide a sector scanner having a large effective sector scan angle.

It is another object of the present invention to provide a sector scanner which has a stationary contact with the object being scanned and is free of vibration problems.

It is still another object of the present invention to provide a sector scanner which has uniform line density and sampling rate at all angles, a high frame rate, and high quality radiating and receiving beam patterns.

It is a further object of the present invention to provide a sector scanner which can provide a simultaneous M-mode or pulsed Doppler scan of any selected line of the sector scan at a high frame rate comparable to conventional M-mode frame rates or pulsed Doppler systems.

It is another object of the present invention to provide a sector scanner which is free of echo artifacts.

It is a further object of the present invention to provide a sector scanner in which no part of the body of diagnostic interest lies in the near Fresnel zone of large variations of acoustic intensity.

SUMMARY OF THE INVENTION

An ultrasonic scanner for producing a sector scan in an object to be examined is provided in which one or more ultrasonic transducers traverse an arcuate path with respect to a reflector which is positioned to receive the ultrasonic waves scanning the surface of the reflector from each of the transducers and converge such waves at a point a preselected distance in front of the reflector. In general the ultrasonic waves are converged at a point outside the scanner and inside the object to produce a sector scan in the object having its center at the convergence point. In one embodiment of the scanner, the reflector only partially reflects the ultrasonic waves and an additional stationary transducer is provided which is positioned to produce ultrasonic waves which radiate through the reflector and coincide with one of the lines of the sector scan, thus permitting simultaneous M-mode or pulse Doppler echo information to be obtained in perfect registration with the sector scan lines. Attenuation, absorbtion and anti-reflection means are provided to suppress echo artifacts.

The novel features which are believed to be characteristic of the invention, both as to its organization and its method of operation, together with further objects and advantages thereof, will be better understood from the following description in connection with the accompanying drawings in which a presently preferred embodiment of the invention is illustrated by way of example. It is to be expressly understood, however, that the drawings are for purposes of illustration and description only and are not intended as a definition of the limits of the invention.

BRIEF DESCRIPTION OF THE DRAWINGS

FIG. 3 is a cross-sectional view of the present invention taken along the lines 3—3 of FIG. 2;

FIG. 4 is a perspective view of the present invention illustrating the reflection and convergence of the ultrasonic waves produced by the present invention;

FIG. 5 and FIG. 6 are cross-sectional views of alternative embodiments of the face portion of the present invention taken along the line 2—2 of FIG. 1; and FIG. 7 illustrates a partial reflector utilized in the present invention.

DETAILED DESCRIPTION OF THE INVENTION

Figure 1:
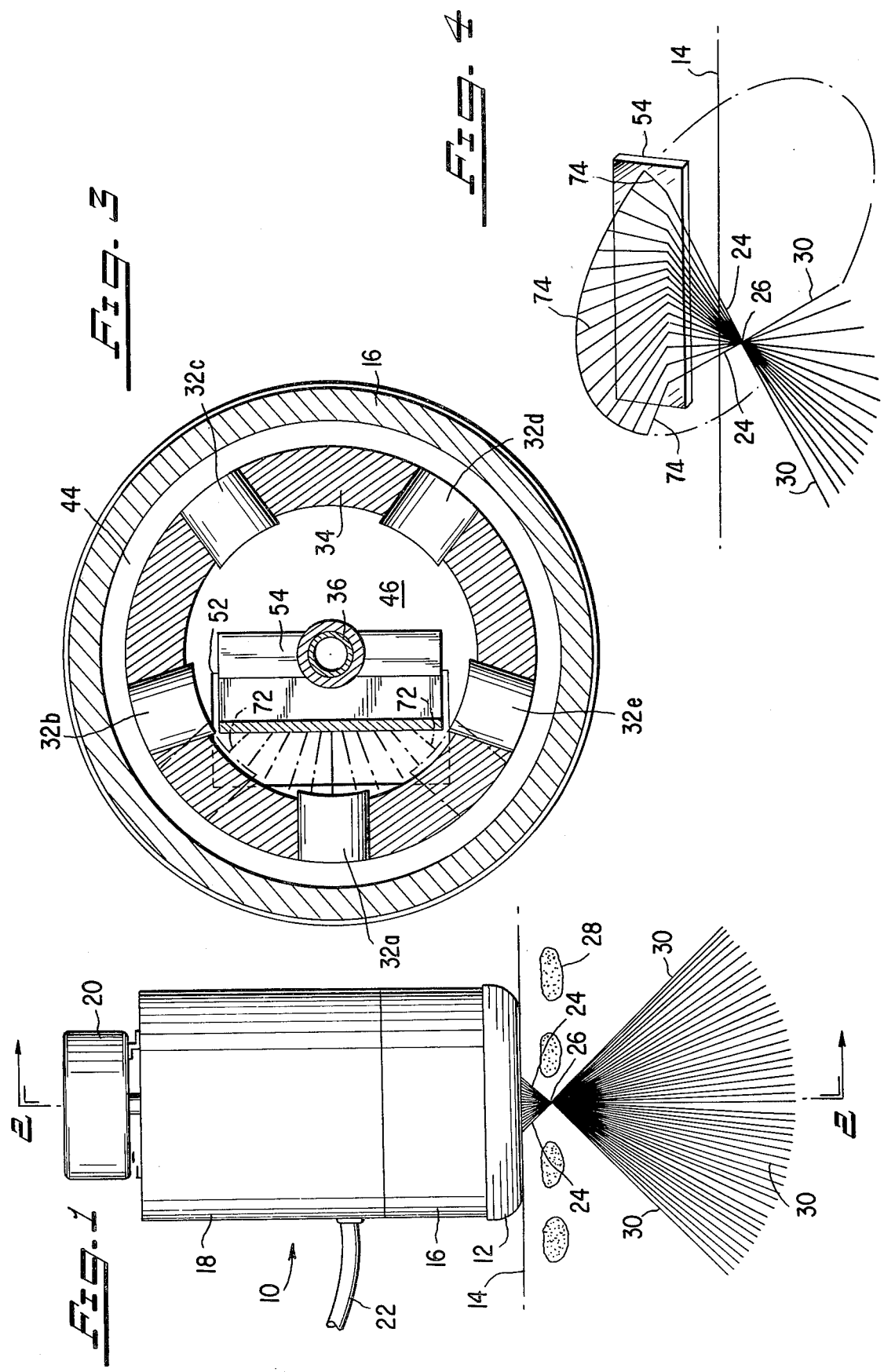
FIG. 1 is a perspective view of a preferred embodiment of the present invention illustrating the sector scan produced within the object to be examined.

Referring now to FIG. 1, a preferred embodiment of the present invention is illustrated. The ultrasonic scanner 10 is shown having a membrane 12 which is placed in contact with the surface 14 of the object to be examined, such as the heart region of the human body. The lower or face portion 16 of the scanner 10 houses the moving ultrasonic transducers and the reflector while the upper portion 18 of the scanner 10 houses the electronics of the scanner 10. A motor 20 is provided on top of the scanner 10 to drive the transducers and a cable 22 provides the electrical power for the various elements of the scanner 10. As is shown in FIG. 1, the ultrasonic waves 24 produced by the scanner 10 converge at a point 26 outside of the scanner 10, between the ribs 28 of the chest of a patient, and then diverge to produce the ultrasonic waves 30 which perform a sector scan of the heart region. The ultrasonic waves 30 are reflected by the various portions of the heart region and are received by the generating transducers and processed in accordance with the pulse-echo method described in the prior art literature referenced herein.

Figure 2:
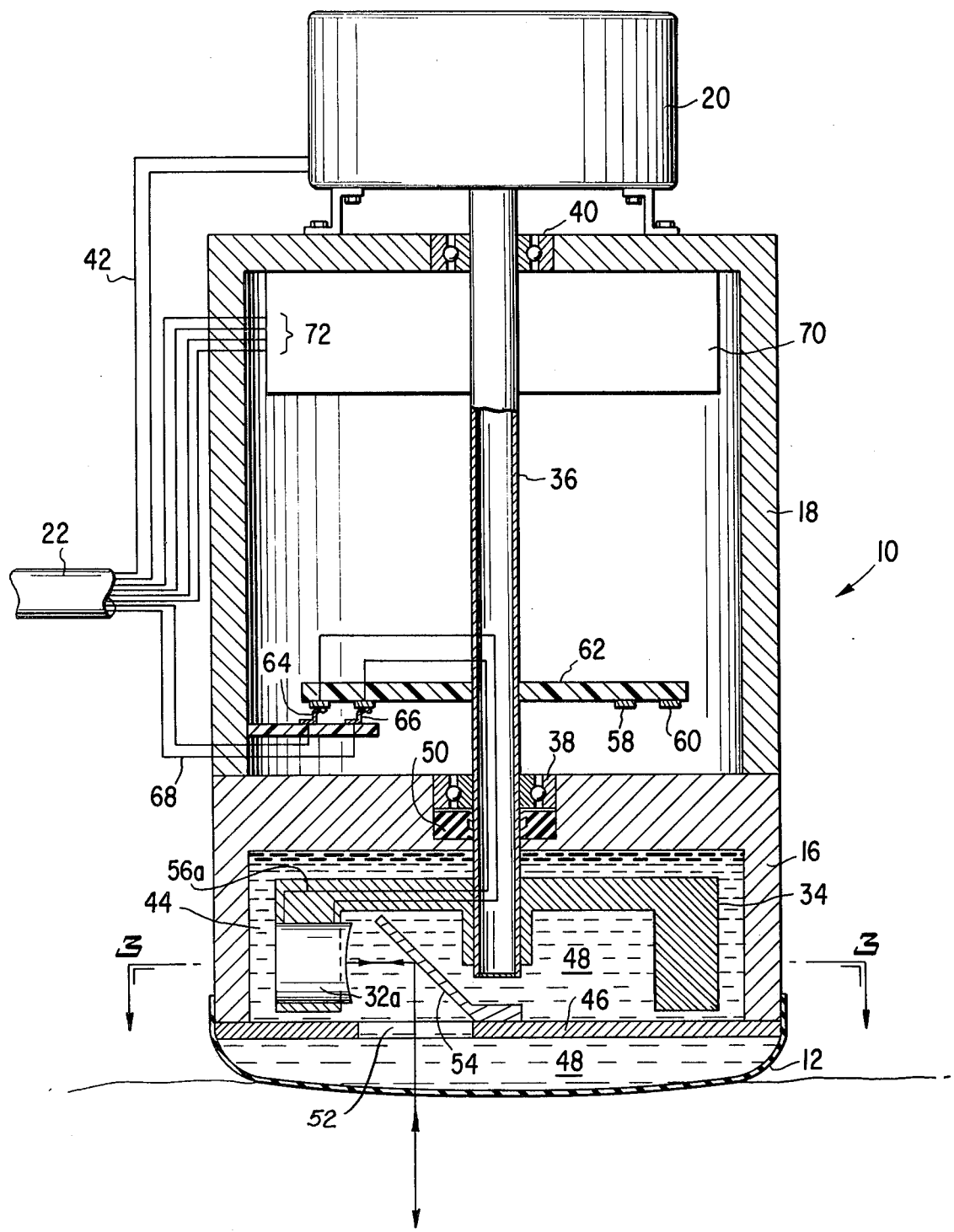
FIG. 2 is a cross-sectional view of the present invention taken along the line 2—2 of FIG. 1.

In FIGS. 2 and 3 a set of ultrasonic transducers 32a–e are shown affixed to ring 34 which is suppored by shaft 36. The shaft 36 is supported by bearings 38 and 40 coupled to the lower portion 16 and the upper portion 18, respectively, of the scanner 10 and is driven by the motor 20 controlled through leads 42. The ring 34 rotates within aperature 44 formed by the lower or face portion 16 and a dividing plate 46 and is immersed in a liquid 48 which is contained by seal 50 and membrane 12, plate 46 being opaque to ultrasonic waves and having an aperature 52 therein to allow ultrasonic waves produced by the transducers 32a-e and reflected off the mirror 54 coupled to the plate 46 to pass through the aperture 52 in the plate 46 and the membrane 12. As stated previously, part of the energy of the ultrasonic waves is reflected by portions of the heart region and returns along the same path to the ultrasonic transducers 32a-e and is detected and displayed as in conventional pulse echo instruments.

The transducers 32a-e are coupled to leads 56a-e which pass through the ring 34 into the hollow center of the shaft 36 and are coupled to slip rings 58, 60 mounted on disc 62 coupled to the shaft 36 and positioned above the transducers 32a-e. The slip rings 58, 60 are cut through at the midpoints between the transducers 32a-e so that the brushes 64, 66 coupled to leads 68 perform a commutating action upon rotation of the shaft 36 and the disc 62 to successively energize the transducers 32a-e and to transmit information received by the transducers 32a-e to the processing equipment. An optical tachometer 70 coupled to leads 72 is affixed to the upper portion 18 and provides an angular reference pulse train of about 500 pulses per shaft revolution in addition to an index pulse once per revolution which is used in conjunction with the pulse train to indicate the angular position of the shaft 36, and hence the position of the transducers 32a-e, at all times, and is also used to servo control the speed of the motor with the pulse rate applied to the transducers 32a-e to produce the ultrasonic waves.

As illustrated in FIGS. 3 and 4, the transducers 32a-e are located on the ring 34 at 72 degree intervals and are sequentially energized in the vicinity of the reflector 54 to produce a series of waves or pulses 74. Due to the constrained circular path of the transducers 32a-e, the ultrasonic waves 74 are directed radially toward the center line of the shaft 36 and scan across the surface of the reflector 54 which is mounted at an angle of 45 degrees with respect to the axis of the shaft 36. Because reflector 54 is located closer to the actuated transducer 32a-e than the radial distance between said transducer and the axis of shaft 36, the ultrasonic waves 74 impinging on the surface of the reflector 54 are reflected through the aperture 52, the fluid 48 and the membrane 12. The emerging ultrasonic waves 24 pass through the surface 14, converge at the point 26 and form a sector scan comprised of waves 30 centered at the intersection of the transducer axis with the shaft axis as projected by the reflector 54 outside the scanner 10. While sector scans can be produced using only one transducer, higher frame rates are achieved by the use of multiple transducers, as described above. The plane of the sector is parallel to the axis of the shaft unless the shaft axis is tilted with respect to the surface of the object being examined and the fluid 48 has a velocity of propagation of sound therein different from the velocity of propagation within the object, in which case the actual angle of the plane is defined by Snell's law, $\sin \theta_2 / \sin \theta_1 = C_2/C_1$ where $\theta_1$ is the angle of incidence, $\theta_2$ the angle of refraction, $C_1$ the velocity of propagation of sound in the incidence medium and $C_2$ the velocity of propagation of sound in the incidence medium and $C_1$ the velocity of propogation of sound in the refracting medium.

The maximum usable sector angle is limited to those angles for which the reflector 54 intercepts substantially all of the ultrasonic beams. Since the distance between the shaft axis and the mirror determines the distance of point 26 from the scanner 10, and since it is desirable for certain applications, such as cardiography, to maintain the point 26, i.e., the effective or projected axis of rotation, within the object, the reflector 54 must be placed sufficiently far from the shaft axis to ensure that the point 26 is within the object. For a hand held device of modest size, however, the maximum scan sector angle is then limited by the mechanical interference of the reflector 54 with the path of the transducers 32a-e as the reflector 54 moves farther from the shaft axis toward the transducers. This limitation can be overcome by using for the fluid 48 a fluid such as an emulsion of toluene in 40% ethanol amine, 60% chloroform, which has a slower velocity of propagation therein than in the object and thus results, by Snell's law, in a larger scan sector angle in the object. As is described more fully hereinafter, the fluid 48 should also have a specific impedance substantially equal to the specific impedance of the object being scanned since multiple reflection artifacts result when a sufficiently large echo results at the interface 14 due to an impedance mismatch. It has been found that fluids with specific impedances of between 1.65 and 1.75 when used in conjunction with a thin latex membrane 12 yield acceptable results and can provide a sector angle of 90 degrees in a human object with a sector angle of 70 degrees within the scanner 10. While the thin elastic membrane enables uneven body contours to be accommodated and the scanner to be tilted to look behind interfering structures, a rigid membrane can be used for industrial applications.

As shown in FIGS. 5 and 6, in order to minimize echo artifacts on reflections from the membrane 12, a flexible membrane may be used, as stated above, made of a material such as latex, together with a window section cut out large enough to accommodate the entire sector scan at the plane of the skin or contact surface 14, with a very thin (eg. 25$\mu$ thick) film 12' of a material such as polyethylene covering the window section. Such a film 12' because it is much less than a wavelength in thickness and has a characteristic impedance not very different than that of the materials on either side of it, will be essentially totally transparent to the ultrasonic radiation. If it is desired to use a more rigid membrane 12, made for example of polyethylene, quarter-wave anti-reflection matching layers 80, 82 composed of low density polyethylene, as shown in FIG. 6, can be used on both surfaces of the membrane 12 to match to the fluid 48 and to the skin or contact surface 14.

In order to reduce the magnitude of those echoes which result at least partly from reflection or scattering from supporting structures within the scanner 10, the transducer ring 34, the portion support 55 of the reflector 54, the plate 46, and the inside surface of the face portion 16, can be made of or covered with a layer 84 of an acoustically highly absorbing material, which has a characteristic impedance $Z_W$ closely matching the characteristic impedance $Z_L$ of the liquid 48, and which may additionally be clad with a quarter-wave anti-reflection matching layer 86, approximately 0.2mm thick and with a characteristic impedance $Z_M \simeq (Z_W Z_L)^{1/2}$.

Since only echo artifacts (but no target echoes) impinge on those internal support structures, the attenuation of the materials may be chosen as high as is feasible without any deleterious effects on the signal strength. A suitable material choice in this case is low-density polyethylene, preferably loaded with carbon, or carbon loaded natural rubber. The material chosen for a matching layer will depend on the liquid selected, and may be composed of a low density polyethylene or an unloaded natural rubber to match a loaded natural rubber wall to castor oil used as the fluid 48.

To further reduce echo artifacts, the fluid 48 can be chosen to be a sound attenuating liquid, such as castor oil, salt solutions such as solutions of hydrated manganese chloride in water, or emulsions such as emulsions of toluene in water which can be made highly attenuating, as described in an article by J. R. Allegra and S. A. Hawley, Journal Acoustical Society of America, Vol. 151, 1972. While the provision of a sound attenuating liquid alone has been found quite effective, there are, however, limits on the values of attenuation coefficient which are acceptable for the liquid 48, because the target echoes must also travel in the liquid 48, and excessive attenuation of those signals must be avoided to maintain a useful signal-to-noise ratio and dynamic range based on signal-to-noise ratio. For example, in order to meet the requirements of having the entire scanned sector or field of view beyond the near Fresnel zone $d^2/8\lambda$ of the transducers 32, where d is the transducer diameter and $\lambda$ is the acoustic wave-length, and achieving a large sector scan angle, within a scanner of minimum external dimensions, the radius of a scanner used in cardiac scanning should be between about 2.5 cm and 3.5 cm, and the corresponding acoustic path length R within the scanner head will be between 2 and 3 cm, with a typical value of 2.5 cm. Pulses leading to target echoes at a range R travel a distance 2R in the liquid 48 and a distance $2R_e = 2R - 2R_i$ in the body or external medium examined. Multiple echo artifacts appearing at range R travel a distance 2R (or nearly 2R for echo artifacts arising from subcutaneous layers) within the liquid 48. Thus, if the attenuation coefficient of the liquid 48 is $\alpha_L$, measured in db/cm, and the average attenuation coefficient of the examined tissue is $\alpha_T$, then the target echoes from range R will suffer an attenuation $A = 2R_i\alpha_L + 2R_e\alpha_T$ on $2R\alpha_T + 2R_i(\alpha_L - \alpha_T)$ whereas multiple echo artifacts will suffer an attenuation (due to the liquid) of about $2R\alpha_L$. Clearly, the larger $\alpha_L$ compared to $\alpha_T$, the greater the attenuation of the multiple echoes with respect to the signal echoes, but also the greater the absolute attenuation of the signal echoes. The excess attenuation $2R_i\alpha_L$ of the signal means a degradation of the system signal-to-noise ratio, for a given transducer input power, efficiency, sensitivity, and preamplifier noise figure. If attenuation in the liquids 48 is used as the sole means of attenuating the basic echo artifacts, and a liquid is chosen that will provide 40 db of attenuation for the multiple echoes at range $2R_i$ (i.e. the first spurious echoes from the membrane 12), then for a typical value $R_i = 2.5$cm, $\alpha_L = 4$ db/cm. The excess attenuation of the target echoes will be 20 db, providing a net reduction of the echo artifacts of 20 db.

In conjunction with an attenuation liquid therefore a layer of a highly absorbing or attenuating solid material 88 may be placed in the primary acoustic path, either on the mirror 54 itself, or immediately adjacent to the transducer 32 or membrane 12. Since it is desirable to provide a scanner 10 which is as small in diameter as is practicable, a suitable absorbing material such as carbon loaded rubber, with an attenuation coefficient as high as 25 db/cm can be utilized, with a layer 2mm thick resulting in a two-way attenuation of 10db. Since the layer 88 should be located so as to intercept (and therefore attenuate) all or nearly all artifactual echoes, and since very close matching of the liquid to the attenuating layer is required to avoid having their interface act as a new source of echo artifacts, location on the transducer 32 is preferred.

In addition to the use of an attenuating layer 88 or liquid 48, it has been found desirable to make the reflector 54 only partially reflecting and of highly acoustically absorbing material so that the portion of the ultrasonic energy which is not reflected by the reflector will be absorbed and not contribute to echo artifacts. The partial reflectivity of the reflector 54 may be achieved by use of a reflector material with a suitable impedance mismatch with the liquid 48. Since, however, this approach can lead to reflectivity which is dependent on the sector scan angle, and requires compensation of the transducer receiver gain (or transmitted power, or both) as a function of scan angle to lead to a uniform display signal strength for a given target echo strength, a suitable partial reflector 54' may be employed, as is shown in FIG. 7, which is comprised of a non-reflecting or weakly reflecting material 90, such as rubber, with narrow, closely spaced (less than a half wave-length) strips 92 of a highly reflecting metal such as tungsten. The use of such a partial reflector 54', attenuating layers 84 and 88, an attenuating liquid 48, and antireflection layers 82 and 86 has resulted in the reduction of echo artifacts, compared to the target echoes and at a range $R_e$ in the examined body of about 3cm or greater, of 20 db, sufficient for artifact-free or substantially artifact-free operation of the scanner of the present invention in medical diagnostic applications.

Since, in order to achieve the echo artifact suppression as described above, the target echoes have also been attenuated by approximately 20 db, it is desirable to use highly efficient transducers 32, and in particular transducers with a relatively high Q-factor. This is, however, contrary to current practice in which pulse excited low efficiency, low (mechanical and electrical) Q transducers are used in order to achieve extremely high range resolution. Since, however, the very short wideband pulses used in the present art scanners become stretched and distorted as they travel through tissues, particularly muscle, because such tissues have a large frequency dependent attenuation, the higher frequency components are resultingly preferentially attenuated, with a resultant effective stretching of the pulse. It has thus, been found that the use of a higher Q transducer with a longer, narrower bandwith pulse results in less distortion and pulse stretching, with the effective lengths significantly greater than those of the low Q, low efficiency transducers.

In FIG. 6 an alternative embodiment of the present invention is shown in which an auxiliary stationary transducer 94 is provided which is positioned in line with one of the ultrasonic waves 24 and behind the partial reflector 54'. The partial reflector 54' has a solid backing 96 with an attenuation similar to the liquid 48 which is coupled to an additional highly absorbing block 98 used to thoroughly dampen the energy which passes through the partial reflector 54. The backing 96 may be composed, for example, of room temperature vulcanized silicone rubber and the block 98 may be composed also of rubber. The transducer 94 is coupled by bracket 100 to block 98 which is coupled to plate 46. Leads 102 are provided to energize transducer 94 and to transmit information received by transducer 94 to the processing equipment. The ultrasonic waves produced by transducer 94 radiate through the partial reflector 54' in coincidence with one of the lines of the sector scan, thus permitting simultaneous M-mode or pulse Doppler echo information to be obtained in perfect registration with the sector scan lines.

Having described the invention, it is obvious that numerous modifications and departures may be made by those skilled in the art; thus the invention is to be construed as limited only to the spirit and scope of the appended claims.

What is claimed is:

1. An ultrasonic scanner comprising:
   a housing;
   reflector means positioned within said housing;
   one or more ultrasonic transducer means moveably mounted within said housing and positioned to direct ultrasonic waves toward and across the surface of said reflector means;
   means for causing said transducer means to traverse an arcuate path with respect to said reflector means, said reflector means positioned closer to said transducer means than the radial distance defined by said arcuate path, and said reflector means angled with respect to said ultrasonic waves, whereby said ultrasonic waves scan across said reflector means and are reflected to converge at a point a preselected distance in front of said reflector means; and
   fluid disposed within said housing for conducting said ultrasonic waves reflected from said reflector means, said fluid having an acoustic propagation velocity substantially less than the acoustic propagation velocity of an object being scanned by said scanner, whereby a larger scan sector angle is obtained in said object.

2. An ultrasonic scanner comprising:
   a housing;
   reflector means positioned within said housing;
   one or more ultrasonic transducer means moveably mounted within said housing and positioned to direct ultrasonic waves toward and across the surface of said reflector means;
   means for causing said transducer means to traverse an arcuate path with respect to said reflector means, said reflector means positioned closer to said transducer means than the radial distance defined by said arcuate path, and said reflector means angled with respect to said ultrasonic waves, whereby the ultrasonic waves scan across said reflector means and are reflected to converge at a point a preselected distance in front of said reflector means; and
   attenuating means for substantially eliminating echo artifacts in said scanner, said attenuating means comprising a layer of absorbing material disposed on preselected surfaces of said scanner and a quarter-wave anti-reflecting layer disposed on said layer of absorbing material.

3. An ultrasonic scanner comprising:
   a housing;
   partial reflector means positioned within said housing;
   one or more ultrasonic transducer means moveably mounted within said housing and positioned to direct ultrasonic waves toward and across the surface of said reflector means;
   means for causing said transducer means to traverse an arcuate path with respect to said reflector means, said reflector means positioned closer to said transducer means than the radial distance defined by said arcuate path, and said reflector means angled with respect to said ultrasonic waves, whereby said ultrasonic waves scan across said reflector means and are reflected to converge at a point a preselected distance in front of said reflector means; and
   stationary transducer means positioned to direct ultrasonic waves through said partial reflector means along a path substantially coincident with said reflected ultrasonic waves.

4. The scanner of claim 3 wherein said partial reflector means comprises a layer of non-reflecting material having a plurality of closely spaced metallic strips thereon.

5. The scanner of claim 1 wherein said reflector means is adapted to partially reflect said ultrasonic waves.

6. The scanner of claim 5 wherein said partial reflector means has an absorbing block coupled thereto for absorbing the ultrasonic waves passing through said partial reflector means.

7. The scanner of claim 5 wherein said partial reflector means comprises a layer of non-reflecting material having a plurality of closely spaced metallic strips thereon.

8. The scanner of claim 1 further comprising attenuating means for substantially eliminating echo artifacts in said scanner, said attenuating means comprising a layer of absorbing material disposed on preselected surfaces of said scanner and a quarter-wave anti-reflecting layer disposed on said layer of absorbing material.

9. The scanner of claim 1 further comprising a membrane adapted to transmit said ultrasonic waves to an object to be scanned, said membrane comprised of a rigid material and having one or more quarter-wave anti-reflecting layers thereon.

10. The scanner of claim 2 further comprising fluid disposed within said housing for conducting said ultrasonic waves reflected from said reflector means, said fluid having an acoustic propagation velocity substantially less than the acoustic propagation velocity of an object being scanned by said scanner, whereby a larger scan sector angle is obtained in said object.

11. The scanner of claim 2 wherein said reflector means is adapted to partially reflect said ultrasonic waves.

12. The scanner of claim 11 wherein said partial reflector means has an absorbing block coupled thereto for absorbing the ultrasonic waves passing through said partial reflector means.

13. The scanner of claim 11 wherein said partial reflector means comprises a layer of non-reflecting material having a plurality of closely spaced metallic strips thereon.

14. The scanner of claim 2 further comprising a membrane adapted to transmit said ultrasonic waves to an object to be scanned, said membrane comprised of a rigid material and having one or more quarter-wave anti-reflecting layers thereon.

15. The scanner of claim 3 wherein said partial reflector means comprises a layer of non-reflecting material having a plurality of closely spaced metallic strips thereon.

16. The scanner of claim 3 further comprising fluid disposed within said housing for conducting said ultrasonic waves reflected from said reflector means, said fluid having an acoustic propagation velocity substantially less than the acoustic propagation velocity of an object being scanned by said scanner, whereby a larger scan sector angle is obtained in said object.

17. The scanner of claim 3 further comprising attenuating means for substantially eliminating echo artifacts in said scanner, said attenuating means comprising a layer of absorbing material disposed on preselected surfaces of said scanner and a quarter-wave anti-reflecting layer disposed on said layer of absorbing material.

18. The scanner of claim 3 further comprising a membrane adapted to transmit said ultrasonic waves to an object to be scanned, said membrane comprised of a rigid material and having one or more quarter-wave anti-reflecting layers thereon.

19. An ultrasonic scanner comprising:
a housing;
reflector means positioned within said housing;
one or more ultrasonic transducer means moveably mounted within said housing and positioned to direct ultrasonic waves toward and across the surface of said reflector means;
means for causing said transducer means to traverse an arcuate path with respect to said reflector means, said reflector means positioned closer to said transducer means than the radial distance defined by said arcuate path, and said reflector means angled with respect to said ultrasonic waves, whereby said ultrasonic waves scan across said reflector means and are reflected to converge at a point a preselected distance in front of said reflector means; and
a membrane adapted to transmit said ultrasonic waves to an object to be scanned, said membrane comprised of a rigid material and having one or more quarter-wave anti-reflecting layers thereon.

20. The scanner of claim 19 wherein said reflector means is adapted to partially reflect said ultrasonic waves.

21. The scanner of claim 20 wherein said partial reflector means has an absorbing block coupled thereto for absorbing the ultrasonic waves passing through said partial reflector means.

22. The scanner of claim 20 wherein said partial reflector means comprises a layer of non-reflecting material having a plurality of closely spaced metallic strips thereon.

23. The scanner of claim 19 further comprising attenuating means for substantially eliminating echo artifacts in said scanner, said attenuating means comprising a layer of absorbing material disposed on preselected surfaces of said scanner and a quarter-wave anti-reflecting layer disposed on said layer of absorbing material.

24. The scanner of claim 19 further comprising fluid disposed within said housing for conducting said ultrasonic waves reflected from said reflector means, said fluid having an acoustic propagation velocity substantially less than the acoustic propagation velocity of an object being scanned by said scanner, whereby a larger scan sector angle is obtained in said object.

25. An ultrasonic scanner comprising:
a housing;
partial reflector means positioned within said housing, said partial reflector means having a backing means coupled thereto;
one or more ultrasonic transducer means moveably mounted within said housing and positioned to direct ultrasonic waves toward and across the surface of said reflector means;
means for causing said transducer means to traverse an arcuate path with respect to said reflector means, said reflector means positioned closer to said transducer means than the radial distance defined by said arcuate path, and said reflector means angled with respect to said ultrasonic waves, whereby said ultrasonic waves scan across said partial reflector means and are partially reflected to converge at a point a preselected distance in front of said reflector means; and
attenuating means for substantially eliminating echo artifacts in said scanner, said attenuating means comprising a fluid having an attenuation coefficient substantially equal to the attenuation coefficient of said backing means.

26. The scanner of claim 25 wherein said partial reflector means comprises a layer of non-reflecting material having a plurality of closely spaced metallic strips thereon.

27. The scanner of claim 25 wherein said fluid has an acoustic propagation velocity substantially less than the acoustic propagation velocity of an object being scanned by said scanner, whereby a larger scan sector angle is obtained in said object.

28. The scanner of claim 25 further comprising a membrane adapted to transmit said ultrasonic waves to an object to be scanned, said membrane comprised of a rigid material and having one or more quarter-wave anti-reflecting layers thereon.

29. An ultrasonic scanner comprising:
a housing;
partial reflector means positioned within said housing, said partial reflector means having a reflectivity substantially less than that of a perfect reflector;
one or more ultrasonic transducer means moveably mounted within said housing and positioned to direct ultrasonic waves toward and across the surface of said reflector means; and
means for causing said transducer means to traverse an arcuate path with respect to said reflector means, said reflector means positioned closer to said transducer means than the radial distance defined by said arcuate path, and said reflector means angled with respect to said ultrasonic waves, whereby said ultrasonic waves scan across said partial reflector means and are partially reflected to converge at a point a preselected distance in front of said reflector means.

30. The scanner of claim 29 further comprising fluid disposed within said housing for conducting said ultrasonic waves reflected from said reflector means, said fluid having an acoustic propagation velocity substantially less than the acoustic propagation velocity of an object being scanned by said scanner, whereby a larger scan sector angle is obtained in said object.

31. The scanner of claim 29 further comprising attenuating means for substantially eliminating echo artifacts in said scanner, said attenuating means comprising a layer of absorbing material disposed on preselected surfaces of said scanning and a quarter-wave anti-reflecting layer disposed on said layer of absorbing material.

32. The scanner of claim 29 further comprising a membrane adapted to transmit said ultrasonic waves to an object to be scanned, said membrane comprised of a rigid material and having one or more quarter-wave anti-reflecting layers thereon.

33. The scanner of claim 29 wherein said partial reflector means comprises a layer of non-reflecting material having a plurality of closely spaced metallic strips thereon.

* * * * *